United States Patent
Zeng

(10) Patent No.: US 10,561,640 B2
(45) Date of Patent: Feb. 18, 2020

(54) TOPICAL PREPARATION FOR SKIN TISSUE PROTECTION AND REPARATION

(71) Applicant: NANJING JIANZHUANG BIOTECHNOLOGY LIMITED COMPANY, Nanjing (CN)

(72) Inventor: Wei Zeng, Nanjing (CN)

(73) Assignee: NANJING JIANZHUANG BIOTECHNOLOGY LIMITED COMPANY, Nanjing (CN)

( * ) Notice: Subject to any disclaimer, the term of this patent is extended or adjusted under 35 U.S.C. 154(b) by 0 days.

(21) Appl. No.: 16/309,935

(22) PCT Filed: Jun. 9, 2017

(86) PCT No.: PCT/CN2017/087748
§ 371 (c)(1),
(2) Date: Dec. 14, 2018

(87) PCT Pub. No.: WO2017/215526
PCT Pub. Date: Dec. 21, 2017

(65) Prior Publication Data
US 2019/0160044 A1    May 30, 2019

(30) Foreign Application Priority Data
Jun. 15, 2016   (CN) .......................... 2016 1 0423398

(51) Int. Cl.
| | | |
|---|---|---|
| A61K 31/4166 | (2006.01) |
| A61Q 19/00 | (2006.01) |
| A61K 8/86 | (2006.01) |
| A61K 47/10 | (2017.01) |
| A61K 31/352 | (2006.01) |
| A61P 17/02 | (2006.01) |
| A61P 17/00 | (2006.01) |
| A61K 31/727 | (2006.01) |
| A61K 8/37 | (2006.01) |
| A61K 8/49 | (2006.01) |
| A61K 33/30 | (2006.01) |
| A61K 9/00 | (2006.01) |
| A61P 17/16 | (2006.01) |
| A61K 47/02 | (2006.01) |

(52) U.S. Cl.
CPC ............ *A61K 31/4166* (2013.01); *A61K 8/37* (2013.01); *A61K 8/49* (2013.01); *A61K 8/494* (2013.01); *A61K 8/498* (2013.01); *A61K 8/86* (2013.01); *A61K 9/0014* (2013.01); *A61K 31/352* (2013.01); *A61K 31/727* (2013.01); *A61K 33/30* (2013.01); *A61K 47/02* (2013.01); *A61K 47/10* (2013.01); *A61P 17/00* (2018.01); *A61P 17/02* (2018.01); *A61P 17/16* (2018.01); *A61Q 19/00* (2013.01)

(58) Field of Classification Search
CPC ...... A61K 31/4166; A61K 8/86; A61K 47/10; A61K 31/352; A61K 31/727; A61K 8/37; A61K 8/49; A61K 33/30; A61K 9/0014; A61K 8/494; A61K 8/498; A61K 47/02; A61Q 19/00; A61P 17/02; A61P 17/00; A61P 17/16
See application file for complete search history.

(56) References Cited

U.S. PATENT DOCUMENTS

| | | | |
|---|---|---|---|
| 7,285,570 B2 * | 10/2007 | Robinson ................. | A61K 8/40 424/400 |
| 2002/0160064 A1 * | 10/2002 | Zulli ...................... | A61K 8/498 424/757 |
| 2010/0278793 A1 * | 11/2010 | Gueniche ................. | A61K 8/99 424/93.42 |

FOREIGN PATENT DOCUMENTS

| | | |
|---|---|---|
| CN | 1310610 A | 8/2001 |
| CN | 102631385 A | 8/2012 |
| CN | 104127403 A | 11/2014 |
| WO | WO 2011049629 | * 4/2011 |

OTHER PUBLICATIONS

Yan Dongliang, Study on effect and mechanism of Cajanus cajan leaf on acute radiation dermatitis, Medicine & Public Health, China Master's Theses Full-Text Database, Oct. 15, 2012, E507-484, pp. 17-20.

Qiao Hongli, Current Situation of the mechanism and the Prophylaxis and Management of Acute Radiation-induced Skin Damage, Proceedings of the 5th International Symposium of Traditional Chinese Medicine, and Combination of Traditional Chinese Medicine and Western Medicine and the 14th National Symposium of Combination of Traditional Chinese Medicine and Western Medicine, Jul. 18, 2014, pp. 1673-1679.

\* cited by examiner

*Primary Examiner* — Shirley V Gembeh
(74) *Attorney, Agent, or Firm* — Gokalp Bayramoglu

(57) ABSTRACT

The present invention relates to a topical preparation for skin tissue protection and reparation. The complex preparation includes the following components: (1) polyethylene glycol; (2) water; and (3) flavonoid compound. The complex preparation may: (1) repair skin injury or promote wound healing; (2) eliminate scars; (3) prevent or treat skin injury caused by radiotherapy; and (4) prevent or treat radiodermatitis.

10 Claims, 2 Drawing Sheets

TOPICAL PREPARATION FOR SKIN TISSUE PROTECTION AND REPARATION

CROSS REFERENCE TO RELATED APPLICATIONS

This application is the national phase entry of International Application No. PCT/CN2017/087748, filed on Jun. 9, 2017, which is based upon and claims priority to Chinese Patent Application No. 201610423398.9, filed on Jun. 15, 2016, the entire contents of which are incorporated herein by reference.

TECHNICAL FIELD

The present invention belongs to the field of medicine, specifically relating to a topical preparation for skin tissue protection and reparation.

BACKGROUND

Skin tissue, as the natural protective layer of the outermost layer of the human body, often faces serious injury due to various internal and external factors. Common causes of skin injury include the factors such as exogenous wounds, endogenous or exogenous inflammation, immune responses and the like. In addition to accidents that cause skin injury, the treatments of many diseases often result in different skin injuries or scar depositions after the injuries due to the healing process.

The purpose of radiation therapy is to minimize the injuries to normal cells while destroying tumor cells. Considering the harmful side effects of radioactive rays in treating tumor cells, the strength of the side effect depends on the dose of radiation and the sensitivity of the irradiated skin tissue to radioactive rays. When the radioactive rays (whether it is ionizing radiation, such as X-rays or gamma rays, or particle radiation, such as neutron beams or alpha-particle beams) generated during the radiotherapy penetrate the body tissues, the atoms after being bombarded lose their outer electrons, thus generating a large amount of active free radicals inside the cells. These free radicals can interact with biological macromolecules such as DNA, proteins, membrane lipids, etc., disrupting their function and ultimately leading to cell dysfunction or death. The most common side effect of radiotherapy in clinical pathology is the radiation skin injury. In many tumor subtypes with effective radiotherapy (such as head and neck cancer, nasopharyngeal cancer, chest and abdomen tumors, etc.), it is often accompanied by very serious skin injuries. Therefore, radiotherapy protectants are often applied in the clinic before and after radiotherapy to achieve the effect of protecting skin tissue.

The ideal radiotherapy protectants should meet the following requirements:
1) must show significant radiotherapy protection effect;
2) must exhibit a certain degree of radiotherapy protection effect on most organs;
3) must be able to be administered by a good patient compliance route;
4) must have acceptable toxicity and protective time-window effect;
5) both the active ingredient(s) and the preparation complex composition thereof must have good stability;
6) can be widely compatible with other drugs.

For the route of administration, the most acceptable routes of administration should be oral administration, skin administration and intramuscular injection. Moreover, the skin administration can significantly reduce side effects such as hypotension, nausea, etc. as compared with intramuscular injection or oral administration, because the time required for the drug to be absorbed into the circulatory system through the skin is longer than that of the intravenous injection, the time reaching the peak of the blood concentration is also delayed. More importantly, the skin administration has a good compliance for the patient, and the operation is simple, time-saving and labor-saving for the medical staff.

Although the demand for skin tissue protection and reparation preparations used to treat corresponding radioactive inflammation or skin injury caused by radiotherapy is great in clinic, currently, there are no corresponding mature and reliable products available.

SUMMARY

Based on the above problems, the present invention first relates to a complex preparation for skin protection and reparation, the complex preparation includes the following ingredients:
(1) polyethylene glycol;
(2) water; and
(3) flavonoid compound.

In the complex preparation, the polyethylene glycol is:
a mixture of more than one single-component polyethylene glycols having different molecular weights, wherein the molecular weight of the single-component polyethylene glycol is 200-20,000, preferably, the mixture is composed of equal mass of a single-component polyethylene glycol having a molecular weight of 200-400, a single-component polyethylene glycol having a molecular weight of 2000-5000, and a single-component polyethylene glycol having a molecular weight of 6000-10,000.

The flavonoid compound is selected from the group consisting of dihydroflavones, flavanols, isoflavones, and flavonoids; preferably naringenin, liquiritigenin, hesperidin, quercetin, kaempferol, genistein, daidzein, luteolin, apigenin or any combination of two or three thereof.

In the complex preparation, the mass ratio of the polyethylene glycol, the water and the flavonoid compound is 50-80:20-30:2-10.

In a preferred embodiment, the present invention relates to a complex preparation for skin protection and reparation, the complex preparation includes the following ingredients:
(1) polyethylene glycol;
(2) water;
(3) flavonoid compound; and
(4) soluble salt.

The polyethylene glycol is:
a mixture of more than one single-component polyethylene glycols having different molecular weights, wherein the molecular weight of the single-component polyethylene glycol is 200-20,000, preferably, the mixture is composed of equal mass of a single-component polyethylene glycol having a molecular weight of 200-400, a single-component polyethylene glycol having a molecular weight of 2000-5000, and a single-component polyethylene glycol having a molecular weight of 6000-10,000.

The flavonoid compound is selected from the group consisting of dihydroflavones, flavanols, isoflavones, and flavonoids; preferably naringenin, liquiritigenin, hesperidin, quercetin, kaempferol, genistein, daidzein, luteolin, apigenin or any combination of two or three thereof.

The salt includes, but is not limited to, sodium salts, potassium salts, zinc salts; the salt is preferably zinc salts or sodium salts, and more preferably zinc chloride or a hydrated salt thereof, zinc sulfate or a hydrated salt thereof, zinc nitrate or a hydrated salt thereof, sodium chloride or heparin sodium.

In the complex preparation, the mass ratio of the polyethylene glycol, the water, the flavonoid compound and salt is 50-80:20-30:2-10:0.2-2.

In another preferred embodiment, the present invention relates to a complex preparation for skin protection and reparation, the complex preparation includes the following ingredients:

(1) polyethylene glycol;
(2) water;
(3) flavonoid compound; and
(4) heparin sodium and allantoin.

The polyethylene glycol is:

a mixture of more than one single-component polyethylene glycols having different molecular weights, wherein the molecular weight of the single-component polyethylene glycol is 200-20,000, preferably, the mixture is composed of equal mass of a single-component polyethylene glycol having a molecular weight of 200-400, a single-component polyethylene glycol having a molecular weight of 2000-5000, and a single-component polyethylene glycol having a molecular weight of 6000-10,000.

The flavonoid compound is selected from the group consisting of dihydroflavones, flavanols, isoflavones, and flavonoids; preferably naringenin, liquiritigenin, hesperidin, quercetin, kaempferol, genistein, daidzein, luteolin, apigenin or any combination of two or three thereof.

In the complex preparation, the mass ratio of the polyethylene glycol, the water, the flavonoid compound, the heparin sodium and the allantoin is 50-80:20-30:2-10:0.2-2:1-5.

The present invention further relates to a preparation method of the complex preparation for skin protection and reparation, the method includes the steps of:

Step (1) heating the polyethylene glycol to 55° C.-90° C.;
Step (2) dissolving the flavonoid compound in the polyethylene glycol solution;
Step (3) adding water to the polyethylene glycol solution, or first dissolving the salt/heparin sodium/allantoin in the water, then adding the salt solution/heparin sodium solution/allantoin solution to the polyethylene glycol, and after mixing uniformly, cooling to normal temperature.

As needed, the method further includes

Step (4) using a pH buffer to adjust the pH of the system to 6.0-8.0, the pH buffer may be a conventional buffer solution such as sodium citrate buffer, sodium bicarbonate buffer or PBS buffer; preferably sodium bicarbonate buffer.

The present invention further relates to a product obtained by using the complex preparation described above for skin protection/reparation, characterized in that, the product may be a health care product, a cosmetic product or a medicine.

The product is prepared from the complex preparation and the necessary adjuvants, excipients, flavoring agents or combinations thereof.

The present invention further relates to a medicine obtained by using the complex preparation described above for skin protection in radiotherapy, characterized in that, the medicine is prepared from the complex preparation and the necessary pharmaceutical excipients, excipients, protectants, flavoring agents or combinations thereof.

The present invention further relates to a medicine obtained by using the complex preparation described above for preventing or treating radiodermatitis, characterized in that, the medicine is prepared from the complex preparation and the necessary pharmaceutical excipients, excipients, protectants, flavoring agents or combinations thereof.

The present invention further relates to an application of the complex preparation in the preparation of a health care product/cosmetic product/medicine for skin protection/reparation, and the application is specifically to prepare the health care product/cosmetic product/medicine by using the complex preparation and adding necessary adjuvants, excipients, flavoring agents, or combinations thereof.

The present invention further relates to an application of the complex preparation in the preparation of a medicine for skin protection in radiotherapy, and the application is specifically to prepare the medicine by using the complex preparation and adding necessary adjuvants, excipients, protectants, flavoring agents or combinations thereof.

The present invention further relates to an application of the complex preparation in the preparation of a medicine for preventing and/or treating radiodermatitis, and the application is specifically to prepare the medicine by using the complex preparation and adding necessary adjuvants, excipients, protectants, flavoring agents or combinations thereof.

The present invention further relates to a flowing application of the complex preparation or the health care product/cosmetic product or the medicine in:

(1) repairing skin injury or promoting wound healing;
(2) eliminating scars;
(3) preventing or treating radiation skin injury caused by radiotherapy; and
(4) preventing or treating radiodermatitis;

The application is accomplished by applying the complex preparation or the health care product/cosmetic product or the medicine for skin protection and reparation to the patient through oral administration or topical skin administration.

DETAILED DESCRIPTION OF THE EMBODIMENTS

Figure 1:
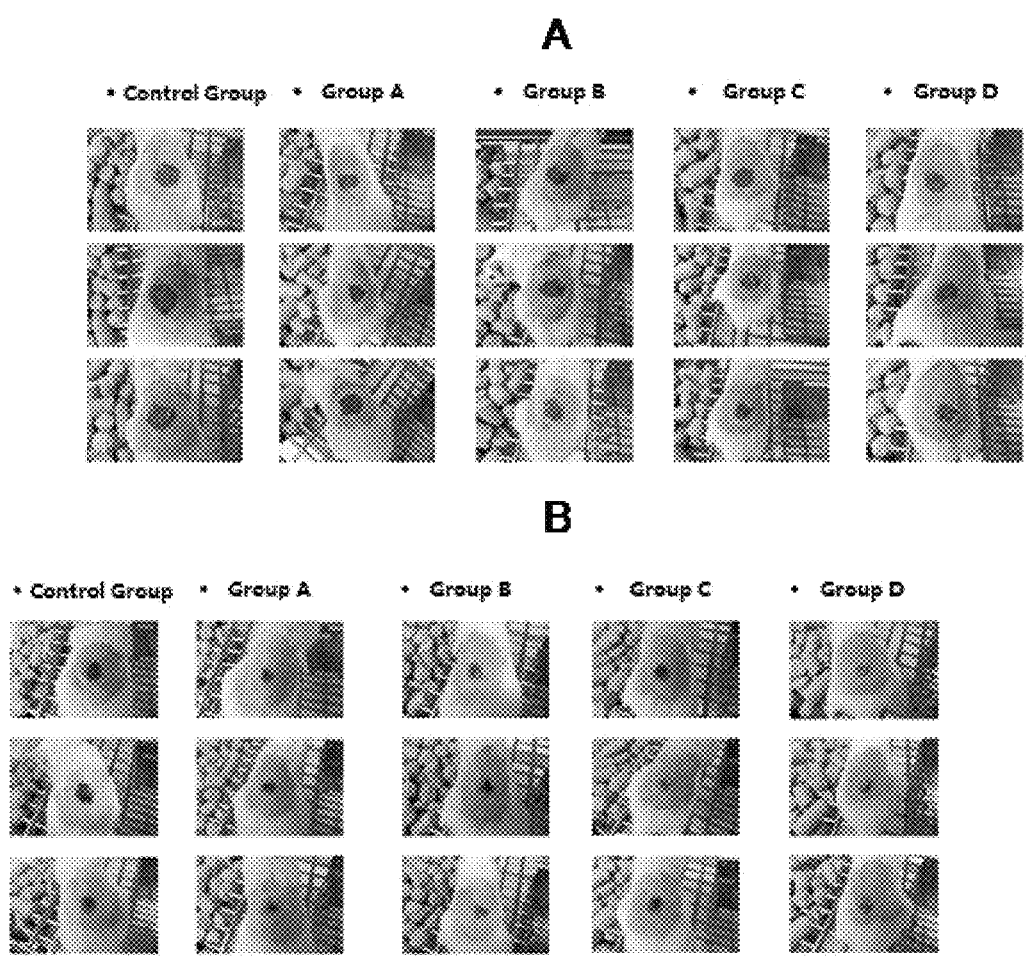
FIG. 1 shows an experiment of an effect of a complex preparation for skin protection and reparation on skin reparation.

Embodiment 1: Preparation of a Complex Preparation for Skin Protection and Reparation Preparation of Formulation 1 (Complex Preparation a):

(1) 150 g PEG200 and 150 g PEG6000 were weighed respectively, mixed well, and heated to 55° C. to obtain a first solution;

(2) 25 g naringenin, 1 g quercetin and 1 g luteolin were weighed respectively, added to the first solution, and fully stirred until completely dissolved to obtain a second solution;

(3) 100 ml water was added to the second solution, fully stirred until completely miscible, and cooled to room temperature to obtain the complex preparation a.

Preparation of Formulation 2 (Complex Preparation b):

(1) 120 g PEG200, 100 g PEG2000 and 150 g PEG5000 were weighed respectively, mixed well, and heated to 75° C. to obtain a first solution;

(2) 25 g naringenin were weighed, added to the first solution, and fully stirred until completely dissolved to obtain a second solution;

(3) 1 g zinc chloride, 0.5 g sodium heparin and 5 g allantoin were weighed respectively, dissolved in 100 g water, and heated or fully stirred until completely dissolved to obtain a third solution;

(4) The second solution and the third solution were uniformly mixed together, cooled to room temperature, and the pH of the mixed solution was adjusted to neutral with sodium citrate to obtain a complex preparation b.

Preparation of Formulation 3 (Complex Preparation c):

(1) 400 g PEG800 was weighed;

(2) 15 g naringenin and 2 g quercetin were weighed respectively, added to the first solution, and fully stirred until completely dissolved to obtain a second solution;

(3) 1 g zinc sulfate was weighed, dissolved in 100 g water, then added to the second solution, fully stirred until completely mixed, and cooled to room temperature to obtain a complex preparation c.

Preparation of Formulation 4 (Complex Preparation d):

(1) 100 g PEG400, 100 g PEG4000 and 100 g PEG8000 were weighed respectively, mixed well, and heated to 75° C. to obtain a first solution;

(2) 20 g naringenin and 5 g quercetin were weighed respectively, added to the first solution, and fully stirred until completely dissolved to obtain a second solution;

(3) 2 g zinc sulfate was weighed, dissolved in 100 g water, then added to the second solution, fully stirred until completely mixed, and cooled to room temperature to obtain the complex preparation d.

Preparation of Formula 5 (Complex Preparation e):

(1) 100 g PEG400, 100 g PEG4000 and 100 g PEG8000 were weighed respectively, mixed well, and heated to 75° C. to obtain a first solution;

(2) 20 g naringenin was weighed, added to the first solution, and fully stirred until completely dissolved to obtain the second solution;

(3) 10 g allantoin and 0.4 g heparin sodium were weighed respectively, dissolved in 100 g water when being heated, and the pH of the mixed solution was adjusted to neutral by adding sodium bicarbonate to obtain a third solution;

(4) The third solution was added to the second solution, fully stirred until completely mixed, and cooled to room temperature to obtain a complex preparation e.

Embodiment 2: Skin Reparation Experiment of Complex Preparation

Experimental Animals and Experimental Methods:

(1) 15 SPF-level Balb/c mice (purchased from Beijing Vital River Laboratory Animal Technology Co., Ltd.) were divided into 5 groups (3 in each group), and kept in an isolated and ventilated constant temperature and humidity environment;

(2) All the back hair of the mice was shaved to expose their back skin, a piece of epidermal tissue of about 4 mm×4 mm in the middle of the back was cut off with sterilized ophthalmic surgical scissors and ophthalmic forceps, iodophor was smeared to disinfect, and this day was set as the 0th day after the wound;

(3) On the 1st day after the wound, no treatment is performed to heal the wound; (4) From the 2nd day after the wound, the medicine was applied topically on the wound on the backs of the mice every day and the reparation condition of the wound was recorded;

Experimental Groups:

Control group: no complex preparation was applied topically, and the wounds of the experimental animals were only self-grown and healed;

Group A: smearing complex preparation e experimental group;

Group B: smearing complex preparation d experimental group;

Group C: smearing complex preparation b experimental group; and

Group D: smearing complex preparation a experimental group.

Images of skin wounds in each group before administration were shown in FIG. 1A, and images of wound recovery on the 9th day were shown in FIG. 1B. It can be seen that in each administration group, the reparation and healing of skin wounds may be well promoted compared with the control group.

Embodiment 3: Complex Preparation for Preventing/Treating Radiodermatitis

Patient Enrollment Conditions:
(1) Patients with bilateral neck radiotherapy; patients enrolled were exposed to the same dose of radiation on both sides of the neck every day;
(2) The starting point of the test investigation started from the appearance of grade I skin injury;
(3) Test investigation indicators:
  a. The time of the appearance of various levels of skin injury (RTOG grading standard)
  b. Whether the test protectant degrades the radiation injury to the unilateral neck skin compared to the control side to which the test protectant is not applied.
  c. The final result is unified after all the patients enrolled have been tested.
(4) Test termination indicators:
  a. Test is suspended if there is skin injury or toxic side reaction greater than/equal to grade III on either side of the two sides.
  b. If skin injuries on both sides are maintained at less than or equal to grade II, the test protectant is applied until the end of radiotherapy;

Smearing method: an appropriate amount of the test protectant is smeared evenly on one side neck skin of the test area expanded outward by about1 cm in the radiation field until it is almost absorbed, the test protectant is smeared twice a day; the other side as a control is not smeared with the test protectant.

Attachment: RTOG evaluation criteria for acute radiation response

Grade 0: almost unchanged;

Grade I: reduced blisters and mild erythema/hair loss/dry desquamation/sweating;

Grade II: marked erythema, and massive wet desquamation/moderate edema;

Grade III: fused wet desquamation other than skin wrinkle part, and pitting edema; and Grade IV: ulcers, bleeding and necrosis.

Two patients with nasopharyngeal carcinoma who received chemotherapy were selected, and the complex preparation was smeared on the patients when a grade I skin injury after the start of radiotherapy appeared. The complex preparation was applied continuously for 7 days. The therapeutic results are shown in Table 1 below.

TABLE 2

Therapeutic Effect of Complex Preparation d on Preventing Radiodermatitis

| Complex Preparation d | | 1st Day | 2nd Day | 3rd Day | 4th Day | 5th Day | 6th Day | 7th Day |
|---|---|---|---|---|---|---|---|---|
| Patient 1 | Smear side | Grade I | Grade I | Grade I | Grade I | Grade I | Grade I | Grade I |
| | Control side | Grade I | Grade II | Grade II | Grade II | Grade II | Grade II | Grade II |
| Patient 2 | Smear side | Grade I | Grade I | Grade I | Grade I | Grade I | Grade I | Grade I |
| | Control side | Grade I | Grade I | Grade I | Grade II | Grade II | Grade II | Grade II |

Figure 2:
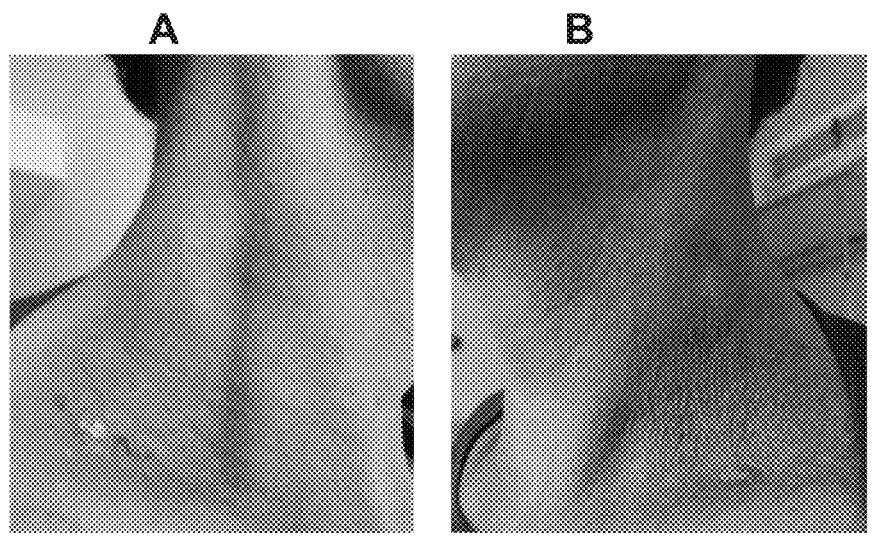
FIG. 2 shows an experiment of an effect of a complex preparation for skin protection and reparation on preventing or treating radiodermatitis.

On the 5th day of treatment, images were taken on the bilateral neck of the patient 2. The results were shown in FIG. 2. It can be seen that the skin of the neck on the control side has marked erythema, the skin at the irradiation point is damaged and no scar was observed (FIG. 2B), while the area of the erythema on the smear side was significantly smaller and the skin injury was already scarred (FIG. 2A). It showed that the complex preparation d has an ideal prevention and therapeutic effects on radiodermatiti s.

Embodiment 4, Complex Preparation for Treating Radiodermatitis

Figure 3:
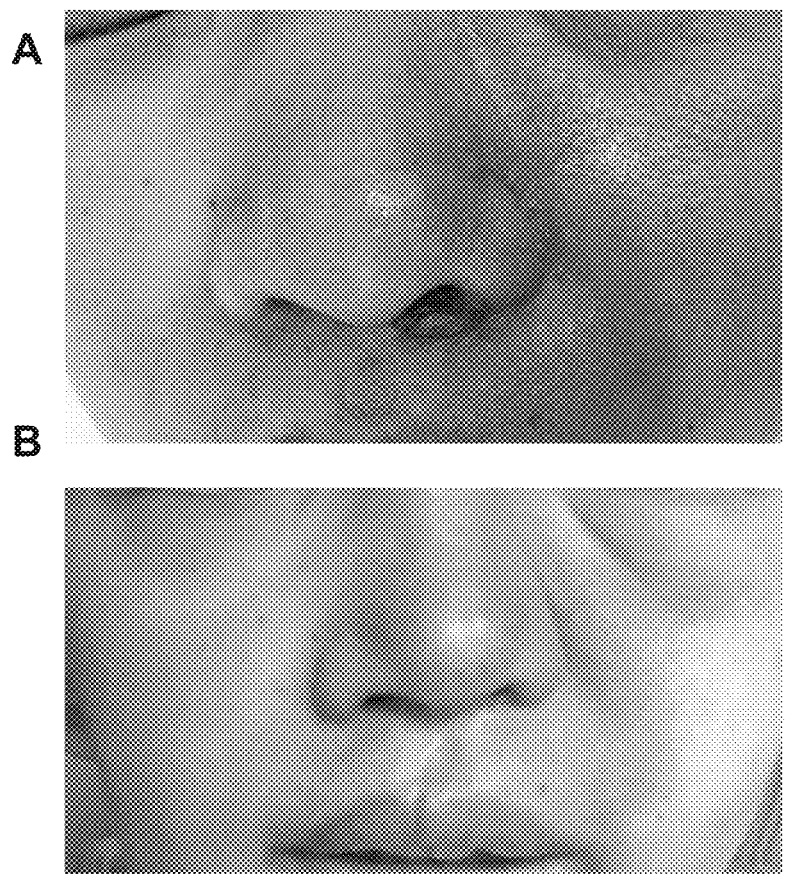
FIG. 3 shows an experiment of an effect of a complex preparation for skin protection and reparation on treating radiodermatitis.

Patient Enrollment Conditions:
(1) Patients with radiodermatitis after the head and neck radiotherapy;
(2) The starting point of the test investigation started from the appearance of grade II skin injury;
(3) Test investigation indicators:
Therapeutic effect of complex preparation on radiodermatitis
(4) Test termination indicators:
a. Test is suspended if there is skin injury or toxic side reaction greater than/equal to grade III on skin surface.
b. The radioactive skin injury indicator is restored to grade 0.
Smearing method: an appropriate amount of the test protectant is smeared evenly on the affected area of radiodermatitis expanded outward by aboutl cm until it is almost absorbed, and the test protectant twice a day.
The images of therapeutic effects of skin inflammation before administration and after 20 days of continuous administration in typical patients enrolled (complex preparation e) are shown in FIG. 3A and FIG. 3B, respectively. The results showed that after applying the complex preparation of the present invention for about three weeks, a good therapeutic effect on radiodermatitis was achieved.
It should be noted that the above embodiments are only used to help the understanding of the essence of the present invention, and are not intended to limit the scope of the present invention.

What is claimed is:
1. A complex preparation for skin protection and reparation, comprising the following ingredients:
   (1) polyethylene glycol;
   (2) water; and
   (3) flavonoid compound;
   wherein, the polyethylene glycol is:
   a mixture composed of equal mass of a single-component polyethylene glycol having a molecular weight of 200-400, a single-component polyethylene glycol having a molecular weight of 2000-5000, and a single-component polyethylene glycol having a molecular weight of 6000-10,000.
2. The complex preparation of claim 1, further comprising the following ingredients:
   (4) soluble salt; and/or
   (5) allantoin.
3. The complex preparation of claim 1, wherein
   the flavonoid compound is one, two or three selected from the group consisting of naringenin, liquiritigenin, hesperidin, quercetin, kaempferol, genistein, daidzein, luteolin, and apigenin;
   the salt is one or more selected from the group consisting of sodium salts, potassium salts, and zinc salts.
4. The complex preparation of claim 1, wherein, in the complex preparation, the mass ratio of the polyethylene glycol, the water, and the flavonoid compound is 50-80 to 20-30 to 2-10.
5. A preparation method of a complex preparation for skin protection and reparation of claim 1, comprising the steps of:
   step (1) heating the polyethylene glycol to 55° C.-90° C. to obtain a polyethylene glycol solution;
   step (2) dissolving the flavonoid compound in the polyethylene glycol solution; and
   step (3) adding water to the polyethylene glycol solution to be a mixed solution, and after mixing the mixed solution uniformly, cooling the mixed solution to normal temperature to be a solution system.
6. The preparation method of claim 5, further comprising:
   step (4) using a pH buffer to adjust the pH of the solution system to 6.0-8.0; wherein, the pH buffer is sodium citrate buffer, sodium bicarbonate buffer or PBS buffer.
7. A product for skin protection and reparation obtained by using the complex preparation of claim 1, wherein
   the product is a health care product/a cosmetic product/a medicine;
   the product is prepared with the complex preparation for skin protection and reparation and adjuvants, excipients, flavoring agents or combinations of the adjuvants, excipients, and flavoring agents; and
   the medicine is:
   (1) a medicine for preventing or treating radiodermatitis; or
   (2) a medicine for treating and preventing skin injury caused by radiation therapy.
8. A preparation method of a complex preparation for skin protection and reparation of claim 2, comprising the steps of:
   step (1) heating the polyethylene glycol to 55° C.-90° C. to obtain a polyethylene glycol solution;
   step (2) dissolving the flavonoid compound in the polyethylene glycol solution; and step (3) first dissolving the salt/allantoin in the water to obtain a salt/allantoin solution, then adding the salt/allantoin solution to the polyethylene glycol to obtain a mixed solution, and after mixing the mixed solution uniformly, cooling the mixed solution to normal temperature to be a solution system.

9. The preparation method of claim 8, further comprising:

step (4) using a pH buffer to adjust the pH of the solution system to 6.0-8.0; wherein, the pH buffer is sodium citrate buffer, sodium bicarbonate buffer or PBS buffer.

10. The product of claim 7, wherein, the complex preparation further comprises the following ingredients:

(4) soluble salt; and/or (5) allantoin.

\* \* \* \* \*